United States Patent
Ninomiya et al.

(10) Patent No.: US 9,381,287 B2
(45) Date of Patent: Jul. 5, 2016

(54) BLOOD FEEDING FLOW RATE-CONTROLLING DEVICE AND EXTRACORPOREAL CIRCULATION DEVICE

(71) Applicants: Hiroshima University, Hiroshima (JP); Josho Gakuen Educational Foundation, Osaka (JP)

(72) Inventors: Shinji Ninomiya, Hiroshima (JP); Taijiro Sueda, Hiroshima (JP); Tatsuya Kurosaki, Hiroshima (JP); Masaaki Kudo, Hiroshima (JP); Naoya Okamura, Hiroshima (JP)

(73) Assignees: Hiroshima University, Hiroshima (JP); Josho Gakuen Educational Foundation, Osaka (JP)

( * ) Notice: Subject to any disclaimer, the term of this patent is extended or adjusted under 35 U.S.C. 154(b) by 127 days.

(21) Appl. No.: 14/383,876

(22) PCT Filed: Jan. 29, 2013

(86) PCT No.: PCT/JP2013/051906
§ 371 (c)(1),
(2) Date: Sep. 8, 2014

(87) PCT Pub. No.: WO2013/132923
PCT Pub. Date: Sep. 12, 2013

(65) Prior Publication Data
US 2015/0045712 A1    Feb. 12, 2015

(30) Foreign Application Priority Data

Mar. 9, 2012 (JP) ................ 2012-053829

(51) Int. Cl.
*A61M 37/00* (2006.01)
*A61M 1/10* (2006.01)
*A61M 1/36* (2006.01)

(52) U.S. Cl.
CPC ............. *A61M 1/1086* (2013.01); *A61M 1/101* (2013.01); *A61M 1/1006* (2014.02);
(Continued)

(58) Field of Classification Search
CPC ... A61M 1/10; A61M 1/1006; A61M 1/1086; A61M 1/3666; A61M 1/3663; A61M 2205/3365
See application file for complete search history.

(56) References Cited

U.S. PATENT DOCUMENTS 4,976,593 A * 12/1990 Miyamoto .............. A61M 1/10
                                                                                417/475
6,048,363 A *  4/2000 Nagyszalanczy ..... A61M 1/101
                                                                                415/900

(Continued)

FOREIGN PATENT DOCUMENTS

EP    0 297 723      8/1993
JP    08-238310      9/1996

(Continued)

OTHER PUBLICATIONS

Okamura, Naoya et al., "Examination of the cardiac load monitoring procedure by using the flow rate-pressure characteristics of centrifugal pump system", Jpn J. Extra-Corporeal Technology, 38(4): 503-505, 2011.

(Continued)

*Primary Examiner* — Leslie Deak
(74) *Attorney, Agent, or Firm* — K&L Gates, LLP; Louis Cullman; Michelle Glasky Bergman

(57) ABSTRACT

A blood supply flow rate controlling device (2), which is a device for controlling the blood supply flow rate in an extracorporeal circulation device connected to a living body (10), includes rotational frequency detecting means that detects the rotational frequency of the centrifugal pump (40) of the extracorporeal circulation device, inlet pressure detecting means and outlet pressure detecting means that detect the inlet pressure and the outlet pressure of the centrifugal pump (40), respectively, flow rate regulating means that regulates a flow rate of blood supplied to the living body by adjusting a flow path cross section area of the blood circulation circuit (20), and controlling means that controls the flow rate regulating means.

5 Claims, 14 Drawing Sheets

(52) U.S. Cl.
CPC .......... *A61M 1/3666* (2013.01); *A61M 1/3639* (2013.01); *A61M 1/3663* (2013.01); *A61M 2205/3351* (2013.01); *A61M 2205/3355* (2013.01); *A61M 2205/3365* (2013.01)

(56) References Cited

U.S. PATENT DOCUMENTS

| 6,808,508 | B1 * | 10/2004 | Zafirelis | A61M 1/101 604/131 |
|---|---|---|---|---|
| 2007/0073393 | A1 | 3/2007 | Kung et al. | |
| 2010/0036486 | A1 | 2/2010 | Mazur | |

FOREIGN PATENT DOCUMENTS

| JP | 08-270595 | 10/1996 |
|---|---|---|
| JP | 09-122228 | 5/1997 |
| JP | 2003-019197 | 1/2003 |
| JP | 2005-058617 | 3/2005 |
| JP | 2005-114764 | 4/2005 |
| JP | 2006-325750 | 7/2006 |
| JP | 2007-140268 | 6/2007 |

OTHER PUBLICATIONS

Extended European Search Report dated Nov. 9, 2015.

* cited by examiner

BLOOD FEEDING FLOW RATE-CONTROLLING DEVICE AND EXTRACORPOREAL CIRCULATION DEVICE

CROSS REFERENCE TO RELATED APPLICATIONS

This application is an application under section 371 of International Application PCT/JP2013/051906 filed on Jan. 29, 2013 which claims priority to Japanese patent application No. 2012-053829 filed on Mar. 9, 2012, the entire disclosures of both of which are incorporated by reference herein.

TECHNICAL FIELD

The present disclosure relates to a blood supply flow rate controlling device and an extracorporeal circulation device.

BACKGROUND ART

Most blood pumps used in open heart surgery or for auxiliary circulation have been constant flow rate pumps exemplified by a roller pump. The roller pump structurally delivers blood in such a way that rotating rollers compress a tube through which blood flows, which thus causes safety problems such as a great loss of blood cells and a risk of foreign material entrainment due to tubing wear.

Given this background, in recent years, a centrifugal pump replacing the roller pump has been increasingly used. The centrifugal pump offers a variety of advantages compared to the roller pump, such as no occurrence of dangerous high pressure, a high level of safety against air entrainment, and no generation of excessive negative pressure.

However, even when the centrifugal pump operates at a constant rotational frequency, the centrifugal pump can cause a blood supply flow rate to be changed upon variation of pressure loading due to narrowing of the patient's blood vessels. An additional flowmeter for sequentially monitoring the blood supply flow rate is thus required to be provided. Also, attempts have been made to keep the blood supply flow rate constant by controlling an arterial line occluder (see, for example, Patent Literature 1) or by controlling the rotational frequency of the centrifugal pump (see, for example, Patent Literatures 2 and 3) under constant monitoring of the flowmeter. As such a flowmeter, an ultrasonic flowmeter or an electromagnetic flowmeter can be used.

CITATION LIST

Patent Literature

Patent Literature 1: Unexamined Japanese Patent Application Kokai Publication No. 2006-325750.
Patent Literature 2: Unexamined Japanese Patent Application Kokai Publication No. H08-238310.
Patent Literature 3: Unexamined Japanese Patent Application Kokai Publication No. H09-122228.

SUMMARY OF INVENTION

Technical Problem

When the flowmeter is installed as in Patent Literatures 1 to 3, the flowmeter yields a measurement error of about 5% and a response lag of about 0.5 sec. The control of the rotational frequency of the centrifugal pump or the control of the occluder is forced to be performed on the basis of the measurement error and the response lag.

Also, when the flow rate is controlled by adjusting the rotational frequency of the centrifugal pump as in Patent Literatures 2 and 3, a reasonable amount of time is required to increase or decrease the rotational frequency of the centrifugal pump to a target value. In addition, even when the rotational frequency is adjusted to the desired value, a certain amount of time is reportedly required for stabilization of the flow rate because of the fluid inertia effect (Rong Weihong et al., "Analysis of Pump Transient during Starting/Stopping Periods by Bond Graph", Transactions of the Japan Society of Mechanical Engineers, Vol. 62, No. 2, pp. 677-683, 1996). In particular, when the rotational frequency is reduced to the target value, significant time delay is caused until the flow rate is reduced. This leads to a disadvantage that the blood supply flow rate is prone to instability.

The present disclosure was made under the above described matters, and an objective of the present disclosure is to provide a blood supply flow rate controlling device and an extracorporeal circulation device that enable the blood supply flow rate to be controlled with high responsivity without use of a flowmeter.

Solution to Problem

According to a first aspect of the present disclosure, a blood supply flow rate controlling device for use in an extracorporeal circulation device connected to a living body, the extracorporeal circulation device including a centrifugal pump for circulating blood through a blood circulation circuit, includes: rotational frequency detecting means that detects a rotational frequency of the centrifugal pump; inlet pressure detecting means and outlet pressure detecting means that detect an inlet pressure and an outlet pressure of the centrifugal pump, respectively; flow rate regulating means that regulates a flow rate of blood supplied to the living body by adjusting a flow path cross section area of the blood circulation circuit; and controlling means that controls the flow rate regulating means, in which the flow rate regulating means is located downstream of the centrifugal pump, the controlling means includes an inputter, a storage, a processor, and an outputter, the inputter receives inputs of a desired target blood supply flow rate entered by an operator, an inlet pressure detection value and an outlet pressure detection value respectively detected by the inlet pressure detecting means and the outlet pressure detecting means, a detected rotational frequency of the centrifugal pump detected by the rotational frequency detecting means, and an estimated blood flow rate equation for calculating an estimated blood flow rate of blood passing through the blood circulation circuit from the inlet pressure detection value, the outlet pressure detection value, and the detected rotational frequency, the storage stores the target blood supply flow rate, the inlet pressure detection value, the outlet pressure detection value, the detected rotational frequency, and the estimated blood flow rate equation, the processor calculates a differential pressure by subtracting the inlet pressure detection value from the outlet pressure detection value, calculates the estimated blood flow rate from the differential pressure and the detected rotational frequency by the estimated blood flow rate equation, and calculates a flow rate differential by subtracting the estimated blood flow rate from the target blood supply flow rate, and the outputter outputs to the flow rate regulating means a control signal that reduces the flow path cross section area when the flow rate differential has a negative value, outputs to the flow rate regulating means a control signal that increases the flow path cross section area when the flow rate differential has a positive value, and outputs to the flow rate regulating means a control signal that reduces the flow path cross section area to zero when the estimated blood flow rate has a negative value.

Preferably, the estimated blood flow rate equation can be expressed by the following equation 1:

$$Qe(f)=\alpha(f)\cdot \Delta P+\beta(f) \quad \text{(equation 1)}$$

where Qe is the estimated blood flow rate, f is the detected rotational frequency of the centrifugal pump, ΔP is the differential pressure by subtracting the inlet pressure detection value from the outlet pressure detection value, and α and β are respectively a slope and an intercept of a linear function of the flow rate of the centrifugal pump as a function of the differential pressure ΔP at the rotational frequency of the centrifugal pump.

Also, the outputter can output to the flow rate regulating means a control signal that reduces the flow path cross section area to zero when the estimated blood flow rate is above a predetermined threshold flow rate.

In addition, the blood supply flow rate controlling device can include a display that displays the target blood flow rate and the estimated blood flow rate, and can be operated using a power supply independent of the power supply to the centrifugal pump.

According to a second aspect of the present disclosure, an extracorporeal circulation device includes the blood supply flow rate controlling device according to the first aspect of the present disclosure.

Advantageous Effects of Invention

A blood supply flow rate controlling device of the present disclosure estimates the flow rate of blood passing through a blood supply line on the basis of a differential pressure between the inlet pressure and the outlet pressure of an centrifugal pump and the rotational frequency of the centrifugal pump, and then controls the blood supply flow rate. No use of a flowmeter and no control of the rotational frequency of the centrifugal pump lead to a highly responsive control of the blood supply flow rate and thus increase safety, compared to a conventional scheme of controlling the rotational frequency of the centrifugal pump on the basis of the feedback of the flowmeter.

BRIEF DESCRIPTION OF DRAWINGS

FIG. 3A shows a state in which an arterial line is opened; FIG. 3B shows a state in which the arterial line is partially closed; and FIG. 3C shows a state in which the arterial line is fully closed;

DESCRIPTION OF EMBODIMENTS

A blood supply flow rate controlling device according to an embodiment of the present disclosure is a device for controlling the blood supply flow rate in an extracorporeal circulation device using a centrifugal pump. The blood supply flow rate controlling device can be later connected to the existing extracorporeal circulation device, or also incorporated into an extracorporeal circulation device to be provided as an integrated extracorporeal circulation device.

The extracorporeal circulation device is a generic name for a device that performs a series of operations to artificially withdraw blood out of a body, manipulate the blood through a blood circuit, and return the blood into the body by a centrifugal pump, a roller pump, and the like. Examples of the extracorporeal circulation devices include an artificial heart-lung machine, a hemodialysis machine, and an apheresis machine. Here, an example of the blood supply flow rate controlling device that is incorporated into the artificial heart-lung machine operable to oxygenate blood withdrawn from a living body (patient) and return the oxygenated blood to the living body during open heart surgery will be explained. Note that the blood supply flow rate controlling device can also be later connected to the existing artificial heart-lung machine as an independent device. In addition, the blood supply flow rate controlling device according to an embodiment of the present disclosure is not limited to the application to the artificial heart-lung machine, but can be utilized in any other extracorporeal circulation devices that use the centrifugal pump.

Figure 1:
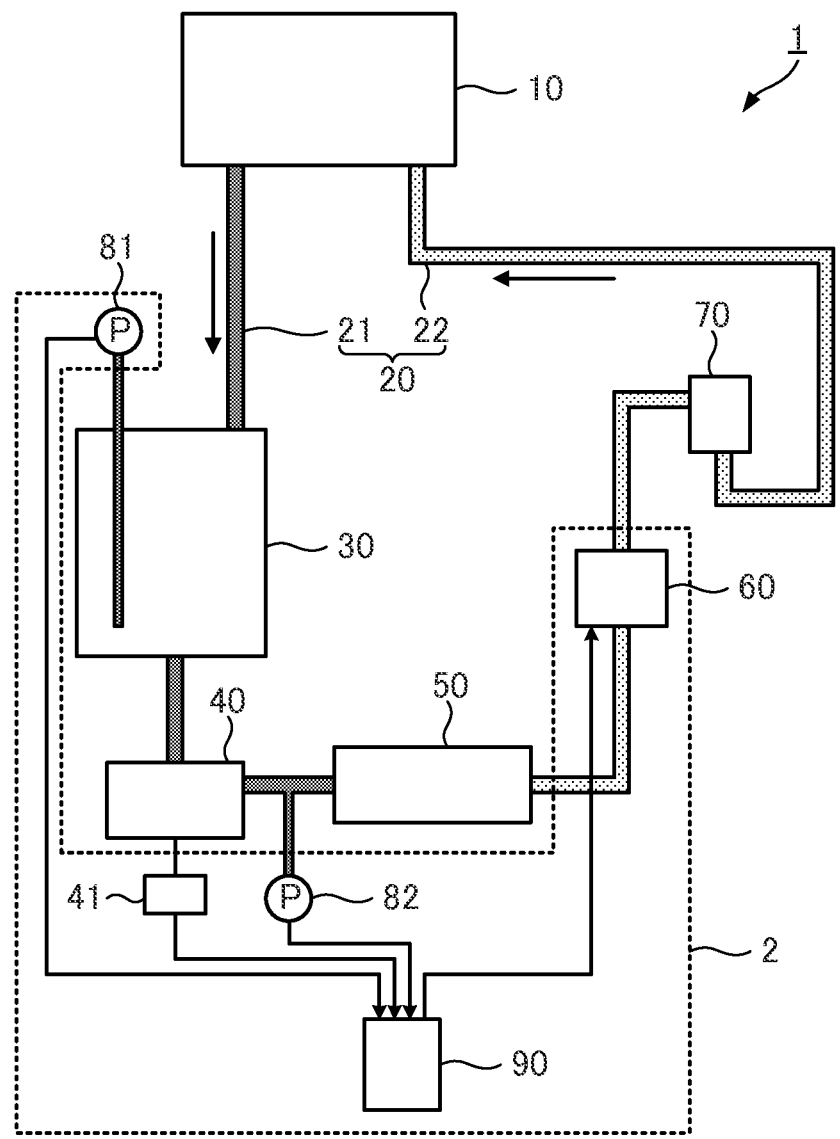
FIG. 1 is a schematic block diagram illustrating an artificial heart-lung machine and a blood supply flow rate controlling device.

An artificial heart-lung machine 1 as shown in FIG. 1 includes a blood circulation circuit 20, a reservoir 30, a centrifugal pump 40, an oxygenator 50, and a filter 70. A blood supply flow rate controlling device 2 includes a rotational frequency detector 41 for detecting the rotational frequency of the centrifugal pump 40, an inlet pressure detector 81 and an outlet pressure detector 82 for respectively detecting the inlet pressure and the outlet pressure of the centrifugal pump 40, a flow rate regulator 60 for regulating the flow rate of blood supplied to a living body 10 by adjusting the flow path cross section area of the blood circulation circuit 20, and a controller 90 for controlling the flow rate regulator 60.

The components of the artificial heart-lung machine 1 and the blood supply flow rate controlling device 2 will be explained hereinafter.

The blood circulation circuit 20 uses a hollow tube made of soft biocompatible material. Here, for explanatory purposes, a line of bloodstream from the living body 10 to the oxygenator 50 is called a venous line 21, while a line of bloodstream from the oxygenator 50 to the living body 10 is called an arterial line 22.

The reservoir 30 is placed in the venous line 21, and stores blood withdrawn from the living body 10. The reservoir 30 is a chamber designed to adjust blood volume in extracorporeal circulation and to remove gas bubbles entrained in the venous line 21.

The centrifugal pump 40 is used for circulating blood via the blood circulation circuit 20. The centrifugal pump 40 is placed downstream of the reservoir 30 and upstream of the oxygenator 50. The centrifugal pump 40 is a pump for providing rotational force to blood and pumping the blood by utilizing the centrifugal force. No valve mechanism in the centrifugal pump 40 offers such advantages as reduced blood loss compared to a roller pump or the like.

The rotational frequency detector 41 comprises a sensor such as an infrared sensor or a Hall sensor, and detects the rotational frequency of the centrifugal pump 40. Moreover, the above rotational frequency detector 41 may not be provided when the rotational frequency can be detected by a pulse signal or a voltage signal provided from a sensor previously provided in the centrifugal pump 40.

The inlet pressure detector 81 is placed upstream of the centrifugal pump 40, and detects pressure at the inlet side of the centrifugal pump 40. The reservoir 30 commonly used has a sampling port for measuring withdrawn blood pressure, so that it is sufficient for the inlet pressure detector 81 to be placed in the sampling port.

Also, the outlet pressure detector 82 is placed downstream of the centrifugal pump 40, and detects pressure at the outlet side of the centrifugal pump 40. The outlet pressure detector 82 is placed downstream of the centrifugal pump 40 and upstream of the flow rate regulator 60. For prompt and accurate estimation of the flow rate, the outlet pressure detector 82 is preferably placed near the outlet of the centrifugal pump 40.

Pressure transducers for blood circuits, pressure sensors disposed via pressure couplers and the like can be used as the inlet pressure detector 81 and the outlet pressure detector 82.

An oxygenator 50 is a device designed to perform gas exchange by oxygenating the withdrawn blood to change venous blood to arterial blood.

The filter 70 is placed in the arterial line 22 downstream of the oxygenator 50. The filter 70 is also referred to as an arterial line filter, and serves to remove any possibly entrained foreign materials or gas bubbles in blood.

The flow rate regulator 60 is placed in the blood circulation circuit 20 downstream of the centrifugal pump 40, and preferably in the arterial line 22 downstream of the oxygenator 50. The flow rate regulator 60 opens and closes the flow path stepwise by changing the flow path cross section area of the arterial line 22 in accordance with the control signals from the controller 90 in order to regulate the flow rate of blood supplied to the living body 10. The flow rate regulator 60 can adopt any mechanism if the flow rate regulator 60 can perform the same kind of function. Generally, a device referred to as an arterial line occluder or a vascular occluder can be used.

In addition, when the filter 70 is placed in the arterial line 22, the filter 70 is preferably placed downstream of the flow rate regulator 60. If the flow rate regulator 60 forms blood clots, the filter 70 can trap the clots, thus enhancing safety.

Figure 2:
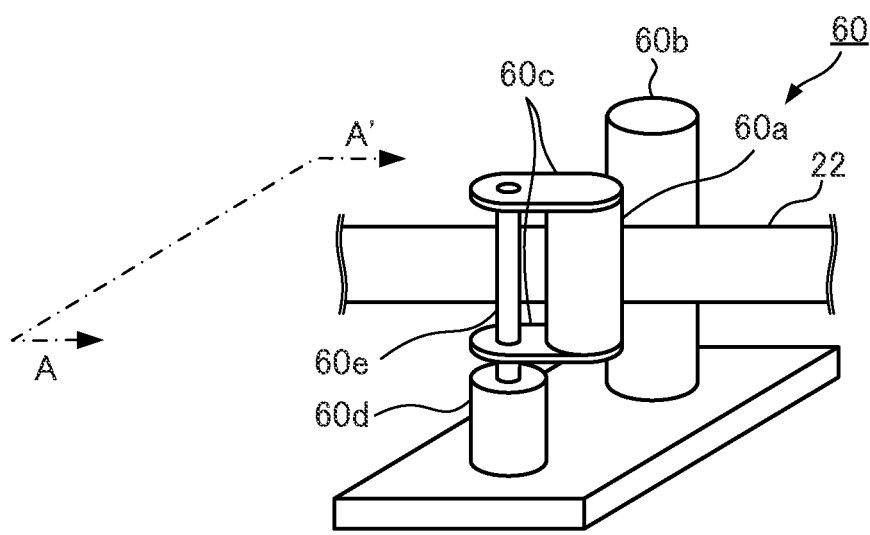
FIG. 2 is a perspective view of a flow rate regulator.

FIG. 2 shows an example of the flow rate regulator 60 that can adjust the internal cross section area of the arterial line 22 by compressing the arterial line 22 stepwise. The flow rate regulator 60 includes a pivoting member 60a, a fixed member 60b, connecting members 60c, a drive source 60d, and a rotary shaft 60e. The pivoting member 60a and the fixed member 60b each form a hard cylindrical body and are placed in parallel to the rotary shaft 60e. The pivoting member 60a and the rotary shaft 60e are connected by the connecting members 60c. Rotation of the rotary shaft 60e by the drive source 60d causes the pivoting member 60a to pivot around the rotary shaft 60e. The drive source 60d can be a device with accurate and adjustable rotation angle such as a stepping motor. Also, the arterial line 22 is interposed between the pivoting member 60a and the fixed member 60b.

The operation of the flow rate regulator 60 will now be explained. FIG. 3A shows a state in which the arterial line 22 is not pressed by the pivoting member 60a and the fixed member 60b and thus has a maximum internal cross section area. Rotation of the rotary shaft 60e from the state counterclockwise in the plane of the paper causes the pivoting member 60a to pivot as shown in FIG. 3B. Then, the arterial line 22 is pressed by the pivoting member 60a and the fixed member 60b and thus has a reduced internal cross section area, which results in reduced flow rate of blood passing through the arterial line 22. Additional rotation of the rotary shaft 60e counterclockwise in the plane of the paper causes the pivoting member 60a to further pivot as shown in FIG. 3C. Then, the arterial line 22 is further pressed by the pivoting member 60a and the fixed member 60b, which forces parts of the inner surface of the arterial line 22 into intimate contact with each other. Then, the flow of blood stops. In addition, the arterial line 22 is preferably adapted to be removable from the flow rate regulator 60. This is because even when the arterial line 22 is unintentionally in a fully closed state due to the failure of the flow rate regulator 60, removal of the arterial line 22 by an operator can quickly release the fully closed state.

The controller 90 is connected in electrical communication with the inlet pressure detector 81, the rotational frequency detector 41 of the centrifugal pump 40, the outlet pressure detector 82, and the flow rate regulator 60. The controller 90 includes an inputter, a storage, a processor, an outputter, and a display.

The inputter receives inputs of a desired target blood supply flow rate Qa entered by an operator of the extracorporeal circulation device, an inlet pressure detection value Pin and an outlet pressure detection value Pout detected respectively at the inlet pressure detector 81 and outlet pressure detector 82, and a detected rotational frequency f of the centrifugal pump 40 detected by the rotational frequency detector 41. In addition, the inputter receives an input of an estimated blood flow rate equation for calculating an estimated blood flow rate Qe of the blood circulation circuit 20 from the inlet pressure detection value Pin, the outlet pressure detection value Pout, and the detected rotational frequency f.

The storage stores the contents that the inputter receives.

The processor calculates a differential pressure $\Delta P$ by subtracting the inlet pressure detection value Pin from the outlet pressure detection value Pout. In addition, the processor calculates the estimated blood flow rate Qe from the differential pressure $\Delta P$ and the detected rotational frequency f by the estimated blood flow rate equation. The processor also calculates a flow rate differential $\Delta Q$ by subtracting the estimated blood flow rate Qe from the target blood supply flow rate Qa.

The outputter outputs to the flow rate regulator 60 the control signal that reduces the flow path cross section area of the arterial line 22 when the flow rate differential $\Delta Q$ has a negative value, the control signal that increases the flow path cross section area when the flow rate differential $\Delta Q$ has a positive value, or the control signal that reduces the flow path cross section area to zero when the estimated blood flow rate Qe has a negative value.

The display displays the inlet pressure detection value Pin, the outlet pressure detection value Pout, the differential pressure ΔP, the detected rotational frequency f, the target blood supply flow rate Qa, the estimated blood flow rate Qe, and other indications including an air entrainment alert and a backflow alert to be described below. Also, when a display installed in the artificial heart-lung machine is available, no additional display is required in the controller 90.

The blood supply flow rate controlling device 2 can be configured as a separate device from the artificial heart-lung machine 1. In this instance, desirably, the controller 90 includes a display, and the blood supply flow rate controlling device 2 is operated using another power supply different from the power supply to the centrifugal pump 40. Another power system different from the power system of the centrifugal pump 40 supplies power to the blood supply flow rate controlling device 2. Specifically, the power supply can be realized by incorporating a battery power supply such as a rechargeable battery into the blood supply flow rate controlling device 2, or by connecting an external power supply to the blood supply flow rate controlling device 2. The independent power supply system and control system from a pump driver of the artificial heart-lung machine 1 serves as a safety mechanism to prevent backflow and excessive blood supply even when a power failure occurs or the pump driver fails. In addition, when alternative blood supply means is used (for example, in the situation of hand turning the centrifugal pump), accurate flow rate control can be also achieved.

Figure 4:
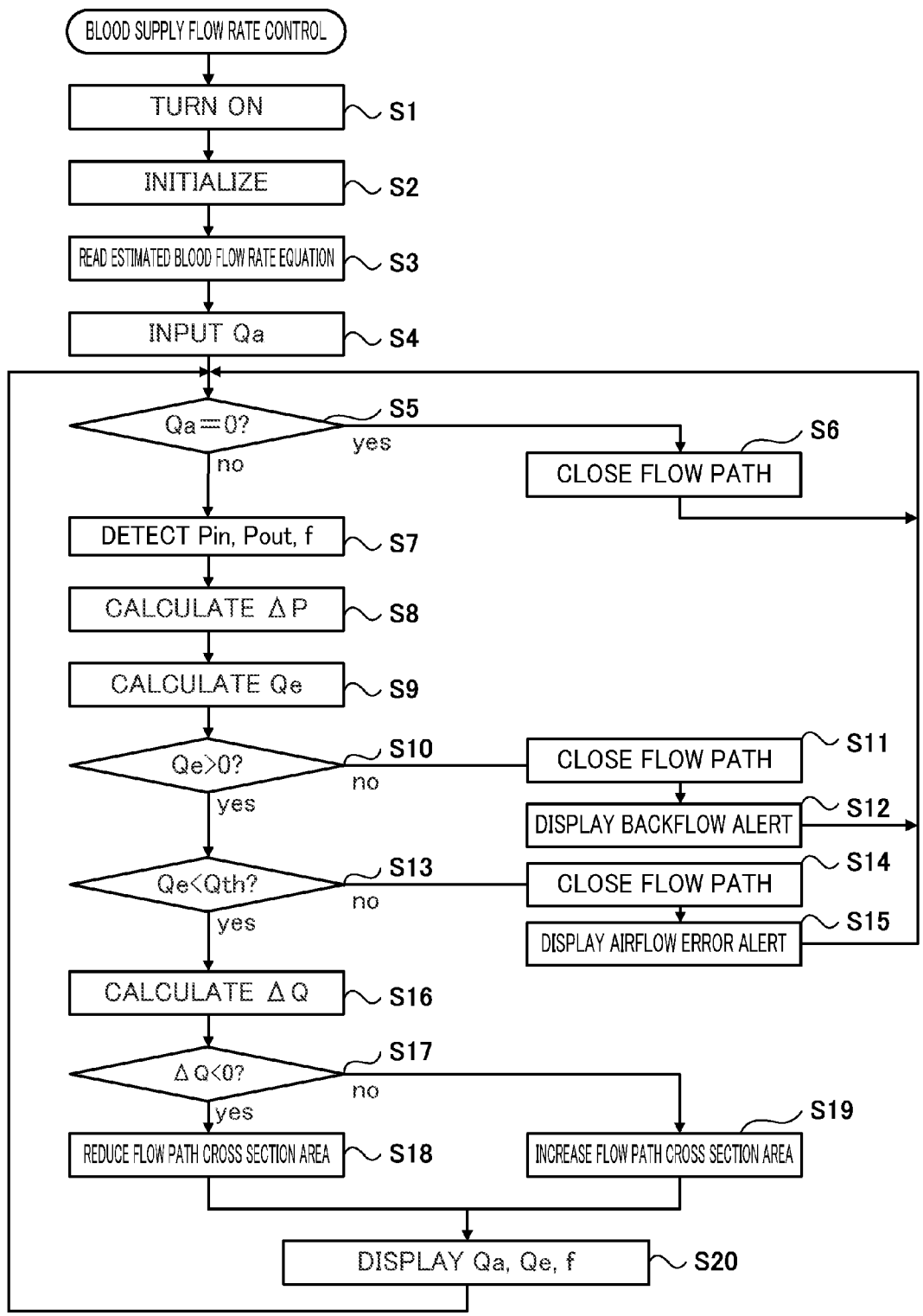
FIG. 4 is a flow diagram showing a procedure for controlling a blood supply flow rate.

Subsequently, a process of controlling the blood supply flow rate will be explained with reference to a flowchart of FIG. 4.

Initially, upon the blood supply flow rate controlling device 2 being turned on (step S1), the controller 90 is initialized (step S2). Next, an estimated blood flow rate equation to be described below is read into the inputter of the controller 90 (step S3), and then the storage stores the equation.

An operator enters a target blood supply flow rate Qa into the inputter of the controller 90 (step S4), and then the storage stores the value. Also, the target blood supply flow rate Qa and the rotational frequency f of a centrifugal pump are set to any value that the operator can select considering information regarding a living body 10, for example, age, symptoms, and sex. The storage of the controller 90 stores each of the values.

Next, a determination is made as to whether the target blood supply flow rate Qa is zero (step S5). If the target blood supply flow rate Qa is zero (step S5: yes), the outputter outputs to the flow rate regulator 60 the control signal that reduces a cross section area of a blood circulation circuit to zero, and then the flow rate regulator 60 operates to fully close the arterial line 22 (step S6). Then, the process loops to step S5.

If the target blood supply flow rate Qa is not zero (step S5: no), the inlet pressure Pin, the outlet pressure Pout, and the rotational frequency f of a centrifugal pump 40 are detected (step S7). These values are input to the inputter of the controller 90, and the storage stores the values.

Then, a processor of the controller 90 calculates a differential pressure ΔP by subtracting the inlet pressure Pin from the outlet pressure Pout (step S8).

Then, the processor calculates an estimated blood flow rate Qe of blood flowing through the blood circulation circuit by the estimated blood flow rate equation (step S9).

The processor determines whether the estimated blood flow rate Qe has a positive value (step S10). If the processor determines that the estimated blood flow rate Qe has a negative value (step S10: no), the outputter outputs to the flow rate regulator 60 the control signal that reduces the cross section area of the arterial line 22 to zero, and then the flow rate regulator 60 fully closes the arterial line 22 (step S11). Then, the display displays a backflow alert (step S12), and the process loops to step S5. The negative value of the estimated blood flow rate Qe means the state in which blood in the blood circulation circuit 20 flows backward. For example, some factors such as the insufficient rotational frequency of the centrifugal pump 40 and the reduced outlet pressure Pout are considered to possibly arise. The flow rate regulator 60 remains the arterial line 22 to be closed until the factors are eliminated.

On the other hand, if the processor determines that the estimated blood flow rate Qe has the positive value (step S10: yes), the processor determines whether the estimated blood flow rate Qe is above a predetermined flow rate threshold Qth (step S13). Here, the flow rate threshold Qth means a threshold of a flow rate that is determined using the estimated blood flow rate equation to be described below based on a differential pressure threshold ΔPth above a differential pressure that is a nominal value of the flow rate of the centrifugal pump 40 at the detected rotational frequency f. For example, the differential pressure threshold Pth can be a value obtained by adding the differential pressure increments, each increment corresponding to an increase in a flow rate of 1 L/min, to the differential pressure that is the nominal value of the centrifugal pump 40 at the detected rotational frequency f. The increment of the differential pressure can be arbitrarily set by an operator and entered into the inputter, and then stored in the storage. The processor calculates the flow rate threshold Qth using the estimated blood flow rate equation.

If the processor determines that the estimated blood flow rate Qe is not below the flow rate threshold Qth (step S13: no), the outputter outputs to the flow rate regulator 60 a control signal that reduces the cross section area of the arterial line 22 to zero, and then the flow rate regulator 60 fully closes the arterial line 22 (step S14). Then, the display displays an airflow error alert (step S15), and the process loops to step S5.

If the processor determines that the estimated blood flow rate Qe is below the flow rate threshold Qth (step S13: yes), the processor calculates a flow rate differential ΔQ by subtracting the estimated blood flow rate Qe from the target blood supply flow rate Qa (step S16).

Next, the processor determines whether the flow rate differential ΔQ has a negative value (step 17). If the flow rate differential ΔQ has a negative value (step S17: yes), the outputter outputs to the flow rate regulator 60 the control signal that causes the flow path cross section area of the arterial line 22 to be reduced. The flow rate regulator 60 operates to reduce the flow path cross section area of the arterial line 22 in accordance with the control signal (step S18). Then, the display displays the target blood supply flow rate Qa, the estimated blood flow rate Qe, and the detected rotational frequency f (step S20), and then the process loops to step S5.

On the other hand, if the processor determines that the flow rate differential ΔQ has a positive value (step S17: no), the outputter provides to the flow rate regulator 60 the control signal that causes the flow path cross section area of the arterial line 22 to be increased. The flow rate regulator 60 operates to increase the flow path cross section area of the arterial line 22 in accordance with the control signal (step S19). Then, the display displays the target blood supply flow rate Qa, the estimated blood flow rate Qe, and the detected rotational frequency f (step S20), and then the process loops to step S5.

As stated above, the blood supply flow rate controlling device 2 sequentially calculates the estimated blood flow rate Qe, and the flow rate of blood flowing through the blood circulation circuit 20 is controlled to be approximate to the target blood supply flow rate Qa.

Subsequently, the calculation of the above mentioned estimated blood flow rate Qe will be explained. The estimated blood flow rate Qe is calculated by the following equation 1:

$$Qe(f) = \alpha(f) \cdot \Delta P + \beta(f) \quad \text{(equation 1)}$$

where Qe is the estimated blood flow rate, f is the detected rotational frequency of the centrifugal pump, $\Delta P$ is the differential pressure calculated by subtracting the inlet pressure detection value Pin from the outlet pressure detection value Pout. Also, $\alpha$ and $\beta$ are respectively a first calibration coefficient and a second calibration coefficient at an arbitrary rotational frequency of the centrifugal pump used. The first calibration coefficient $\alpha$ and the second calibration coefficient $\beta$ respectively represent the slope and the intercept of a linear function of the flow rate Q of the centrifugal pump as a function of a differential pressure $\Delta P$ at an arbitrary rotational frequency of the centrifugal pump used.

Figure 5:
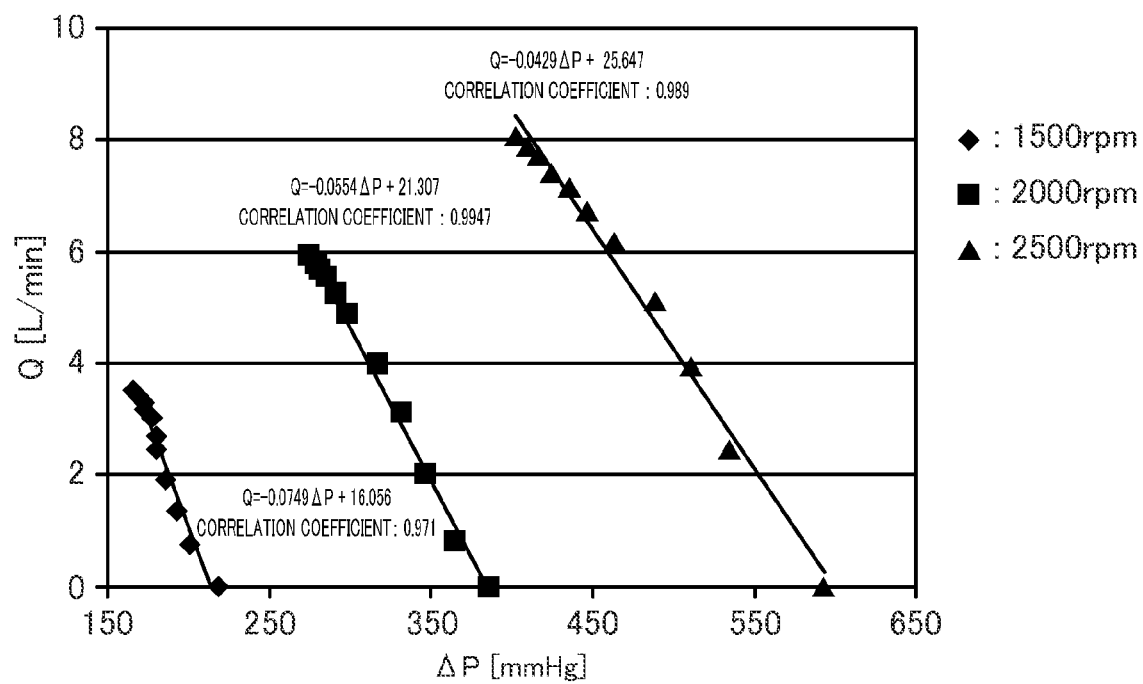
FIG. 5 is a graph showing a relationship between flow rate and differential pressure of a centrifugal pump.

The derivation process of the equation 1 will be explained hereinafter. Initially, the extracorporeal circulation device shown in FIG. 1 was constructed, and pressure gauges were installed each of an outlet of the centrifugal pump and a sampling port of a reservoir. Then, water was circulated through a blood circulation circuit and the flow rate of water flowing therethrough was measured. Capiox® centrifugal pump (from Terumo Corporation) was used as a centrifugal pump. The differential pressures $\Delta P$ were varied by changing afterloads at constant frequencies f of the centrifugal pump of 1500 rpm, 2000 rpm, and 2500 rpm, respectively, and then the changes in flow rate were measured. FIG. 5 shows the result.

Referring to FIG. 5, the relationship between the flow rate Q and the differential pressure $\Delta P$ is nearly linear for all the rotational frequencies f. The straight line fitting of characteristics of the flow rate Q and the differential pressure $\Delta P$ at each of the frequencies f yields the following equations 2 to 4:
(the rotational frequency f of the centrifugal pump: 1500 rpm)

$$Q \text{ (L/min)} = -0.0749 \cdot \Delta P + 16.056 \quad \text{(equation 2)}$$

(the rotational frequency f of the centrifugal pump: 2000 rpm)

$$Q \text{ (L/min)} = -0.0554 \cdot \Delta P + 21.307 \quad \text{(equation 3)}$$

(the rotational frequency f of the centrifugal pump: 2500 rpm)

$$Q \text{ (L/min)} = -0.0429 \cdot \Delta P + 25.647. \quad \text{(equation 4)}$$

Figure 6:
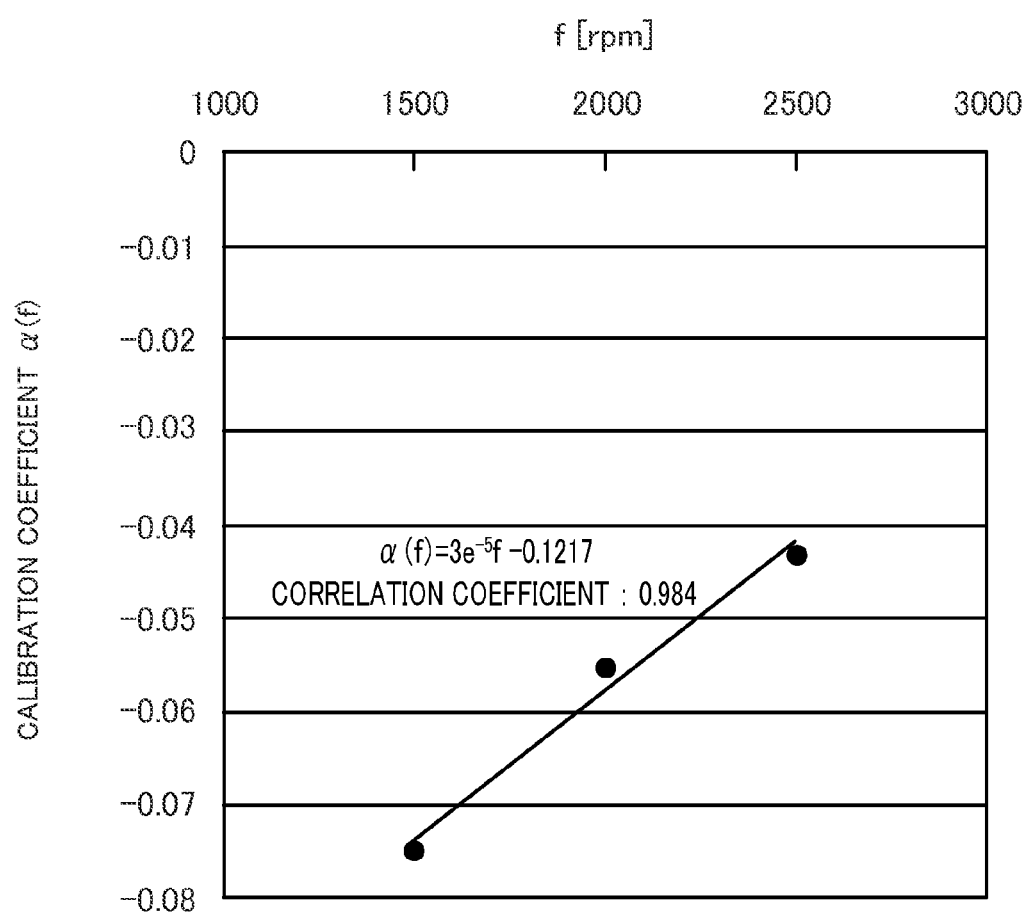
FIG. 6 is a graph showing a relationship between rotational frequency and calibration coefficient α(f) of a centrifugal pump.

Next, each slope $\alpha(f)$ of the equations 2 to 4 is plotted, the result of which is shown in FIG. 6. Referring to FIG. 6, the relationship between the rotational frequency f of the centrifugal pump and the slope $\alpha(f)$ of the equations 2 to 4 is nearly linear. The straight line fitting of the result yields the following equation 5:

$$\alpha(f) = 3e^{-5} \cdot f - 0.1217. \quad \text{(equation 5)}$$

The slope $\alpha(f)$ at an arbitrary rotational frequency f of the centrifugal pump is determined from the equation 5.

Figure 7:
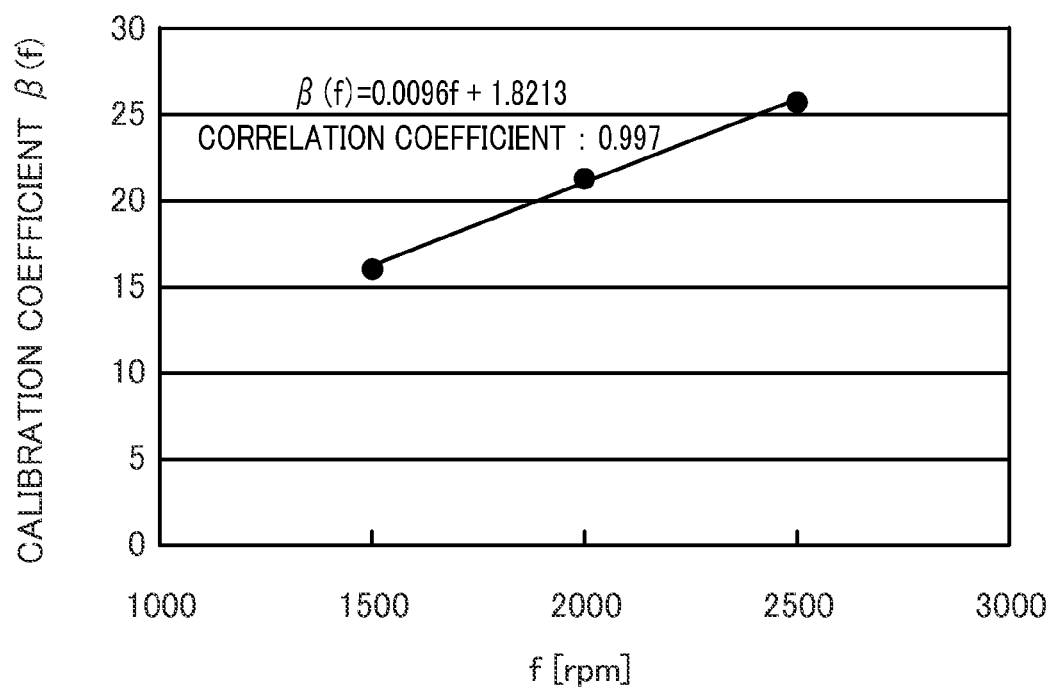
FIG. 7 is a graph showing a relationship between rotational frequency and calibration coefficient β(f) of a centrifugal pump.

In addition, each intercept $\beta(f)$ of the equations 2 to 4 is plotted, the result of which is shown in FIG. 7. Referring to FIG. 7, the relationship between the rotational frequency f of the centrifugal pump and the intercept $\beta(f)$ is nearly linear. The straight line fitting of the result yields the following equation 6:

$$\beta(f) = 0.0096 \cdot f + 1.8213. \quad \text{(equation 6)}$$

The intercept $\beta(f)$ at an arbitrary rotational frequency of the centrifugal pump is determined from the equation 6.

Thus, the equations 5 and 6 yield the first calibration coefficient $\alpha(f)$ and the second calibration coefficient $\beta(f)$ at an arbitrary rotational frequency of the centrifugal pump, that is, at the set rotational frequency of the centrifugal pump. It can be seen that the equation 1 gives the estimated blood flow rate Qe by substituting the first calibration coefficient $\alpha(f)$ and the second calibration coefficient $\beta(f)$ at the set rotational frequencies of the centrifugal pump into the equation 1 and then detecting Pin and Pout to determine the differential pressure $\Delta P$.

Note that the centrifugal force is involved in increasing the pump head on the principle of a centrifugal pump. Energy from the centrifugal force is affected by the fluid mass, and in particular, by the fluid specific gravity when the volume is constant. In addition, the centrifugal pump is affected by the viscosity in a non-trivial way. These influences are preferably considered because the viscosity or any other properties of the circulating blood can change over time.

Figure 8:
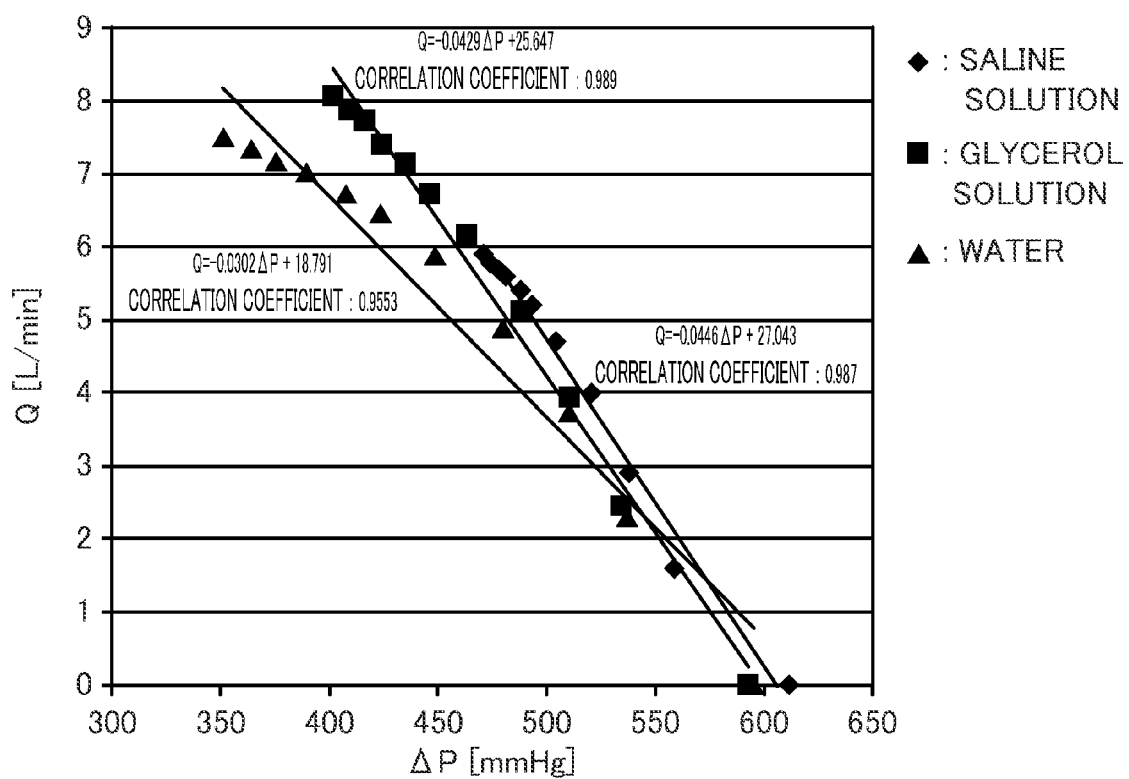
FIG. 8 is a graph showing a relationship between flow rate and differential pressure for various fluids used.

Three kinds of liquids, for example, a saline solution, a glycerol solution and water were examined for characteristics of the flow rate and the differential pressure, the result of which is shown in FIG. 8. The specific gravity and the viscosity of the saline solution, glycerol solution and water used were as follows. Also, the rotational frequency of the centrifugal pump was 2500 rpm for each of the liquids. Note that the typical blood viscosity is substantially similar to the viscosity of the glycerol solution used in this experiment.

(saline solution) specific gravity 1.1, viscosity 1.1 cP
(glycerol solution) specific gravity 1.1, viscosity 2.6 cP
(water) specific gravity 1.1, viscosity 1.0 cP Referring to FIG. 8, the differences of the viscosity result in small shift, and the straight line fitting for each result is given as follows:

$$\text{saline solution: } Q = -0.0446\Delta P + 27.043 \quad \text{(equation 7)}$$

$$\text{glycerol solution: } Q = -0.0429\Delta P + 25.647 \quad \text{(equation 8)}$$

$$\text{water: } Q = -0.0302\Delta P + 18.791. \quad \text{(equation 9)}$$

In particular, the higher flow rate tends to cause the greater shift.

Figure 9:
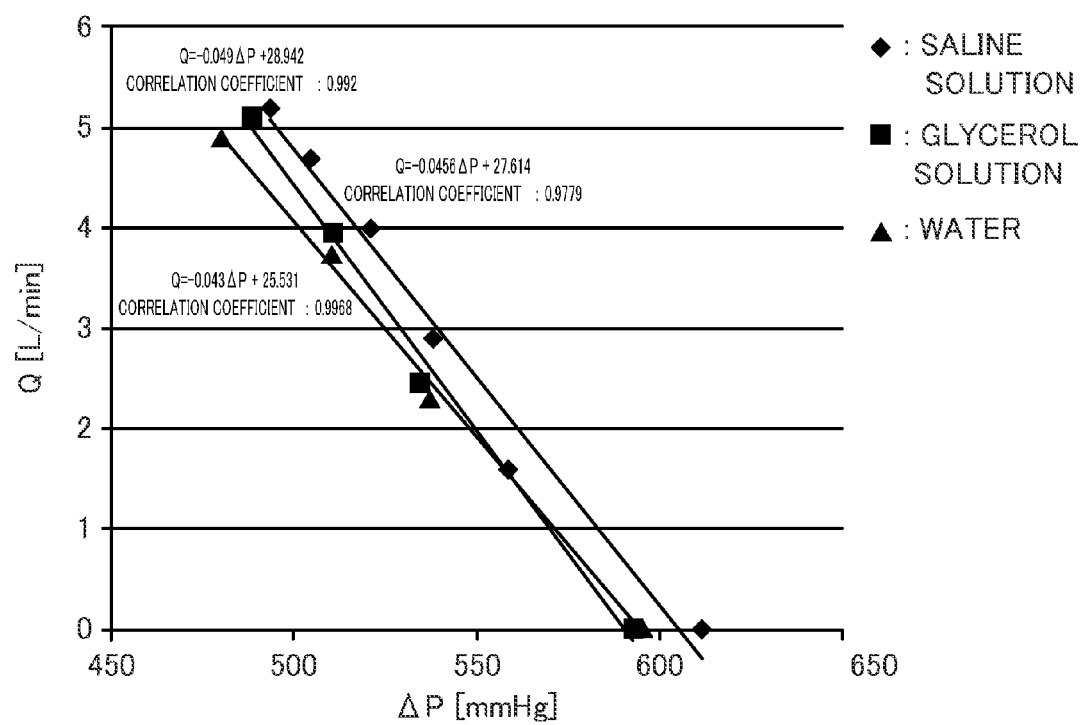
FIG. 9 is a graph showing a relationship between flow rate and differential pressure for various fluids used.

However, open heart surgery is typically conducted using a blood supply flow rate of 5 L/min or less. In light of the circumstances, FIG. 9 shows a graph in a range of a flow rate of 5 L/min or less. Then, the straight line fitting for each result in the range of a flow rate of 5 L/min or less is given as follows:

$$\text{saline solution: } Q = -0.0456\Delta P + 27.613 \quad \text{(equation 10)}$$

$$\text{glycerol solution: } Q = -0.049\Delta P + 28.942 \quad \text{(equation 11)}$$

$$\text{water: } Q = -0.043\Delta P + 25.531. \quad \text{(equation 12)}$$

No significant difference was found among the three liquids in the range of a flow rate of 5 L/min or less. The result shows that, in the range of a flow rate of 5 L/min or less, the blood supply flow rate can be appropriately controlled even with any change in viscosity or any other properties during open heart surgery by measuring the characteristics of the flow rate Q versus the differential pressure $\Delta P$ at a predetermined rotational frequency of the centrifugal pump as described above, determining a first calibration coefficient $\alpha(f)$ and a second calibration coefficient $\beta(f)$ of the equations 5 and 6 respectively from the acquired approximate straight line (a linear function), and substituting the calibration coefficients into the equation 1 to calculate the estimated blood flow rate Qe.

The blood supply flow rate controlling device 2 according to an embodiment of the present disclosure, therefore, controls a blood supply flow rate by adjusting the flow path cross section area of the arterial line 22 without use of a flowmeter and without control of the rotational frequency of the centrifugal pump 40. Control of the rotational frequency of the centrifugal pump 40 is not required, so that the risk of oversupply of blood due to the excessive rotational frequency of the centrifugal pump 40 can be avoided, which provides improved safety.

Further, the flow rate regulator 60 can quickly change the flow path cross section area, thus enabling the quick change in the flow rate. Specifically, a response speed within a human living body regarding vascular controls such as vasodilatation and vasoconstriction by autonomic control might be approximately in the neighborhood of 1 second. The flow rate regulator 60 such as an occluder can change the flow path cross section area within 1 second even when the blood supply flow rate is reduced, so that the effect of reduced burden on the living body can be expected.

Further, the flow rate regulator 60 is controlled in response to the flow rate differential ΔQ between the target blood supply flow rate Qa and the estimated blood flow rate Qe. Thus, for example, when air is entrained in the centrifugal pump 40, the outlet pressure detection value Pout drastically decreases, and thus the differential pressure ΔP drastically decreases. The flow rate regulator 60 is then immediately driven such that the flow path of the blood circulation circuit 20 is fully closed. Therefore, the risk of error of delivering air to the living body can be avoided.

Further, when the estimated blood flow rate Qe is above the threshold flow rate Qth, the flow rate regulator 60 is immediately driven such that the flow path of the arterial line 22 is fully closed. If air is entrained in the centrifugal pump 40, the outlet pressure drastically decreases, thereby producing a larger value for the estimated blood flow rate Qe. Then, when the estimated blood flow rate Qe is above the threshold flow rate Qth, the possibility of the airflow error occurring can be considered, and then the flow path is closed. This further improves the prevention of the error of delivering air to the living body 10.

In addition, when the estimated blood flow rate Qe has a negative value, backflow is considered to have occurred in the blood circulation circuit 20, and then the flow rate regulator 60 controls the flow path cross section area to zero. Therefore, the risk of backflow in the blood circulation circuit 20 can be avoided, which provides improved safety.

Further, the blood supply flow rate controlling device 2 is provided as a separate control device from the pump driver, thus serving as a safety mechanism to prevent backflow and excessive blood supply even when a power failure occurs or the pump driver fails. In addition, when alternative blood supply means is used (for example, in the situation of hand turning the centrifugal pump), accurate flow rate control can be also achieved.

Example 1

The usefulness of controlling an opening of an occluder was examined as a method for controlling a blood supply flow rate in an extracorporeal circuit using a centrifugal pump.

An extracorporeal circuit was constructed using a commercially available centrifugal pump and arterial line occluder, and flow rate response characteristics to variations of the occluder opening were studied. HAS-RE (from Senko Medical Instrument Mfg. Co. Ltd.) was used as an occluder.

The rotational frequency of the centrifugal pump was kept constant (2000 rpm), and then the opening of the occluder was changed stepwise 0% to 100% at 10 sec intervals to change the flow rate.

In addition, as a comparative example, the flow rate response characteristics were studied by not controlling the opening of the occluder but changing the target value of the rotational frequency of the centrifugal pump. In the comparative example, the target value of the rotational frequency of the centrifugal pump was changed stepwise 1000 rpm to 2000 rpm at 10 sec intervals to change the flow rate. The lower limit of the rotational frequency of the centrifugal pump was set to 1000 rpm in order to prevent the occurrence of backflow.

In either case, CAPIOX® SP-101 (from Terumo Corporation) as an centrifugal pump and water (viscosity=about 1 cP) were used as a working fluid.

Figure 10:
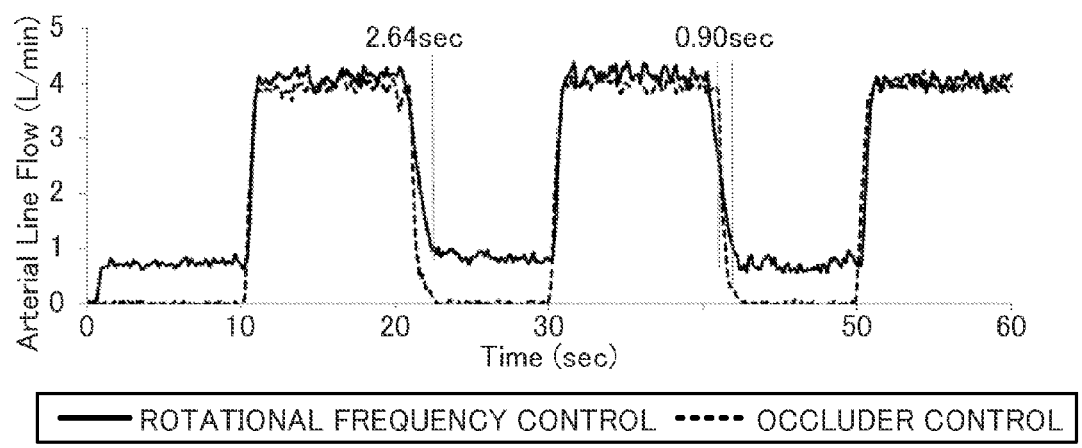
FIG. 10 is a graph showing flow rate response characteristics for an occluder opening control and a rotational frequency control in Example 1.

FIG. 10 shows the result. When the flow rate increased, no differences were observed in the flow rate response characteristics for both the rotational frequency control and the occluder opening control. However, when the flow rate decreased, the time required to reach the flow rate lower limit after the target value of the opening of the occluder had been decreased was about 0.9 sec, while the time required to reach the flow rate lower limit after the target value of the rotational frequency had been decreased was 2.64 sec. This revealed that the control of the rotational frequency of the centrifugal pump caused a response lag of about three times that of the occluder control.

This response lag is influenced by the inertia of the fluid, and the response of the flow rate change of the centrifugal pump to the change in the rotational frequency tends to lag with respect to the response to the change in pressure. This experiment shows that the control of the opening of the occluder is superior in responsivity over the control of the rotational frequency of the centrifugal pump as a method for controlling the flow rate in the extracorporeal circuit using the centrifugal pump.

Further, this experiment revealed that the flow rate control by controlling the rotational frequency of the centrifugal pump caused a response lag of about 2 to 3 sec with respect to the control of the occluder opening when the target value of the flow rate had been decreased in the extracorporeal circuit. This response lag makes the prevention of backflow difficult. The control of the occluder opening is found to be superior over the method for controlling the rotational frequency of the centrifugal pump in view of the backflow prevention. Therefore, in this application, the estimated blood flow rate can be calculated using as input values the pressure and the rotational frequency that can be detected with a shorter response lag, and also the flow path cross section area can be quickly changed by the occluder on the basis of the estimated blood flow rate. This enables quick change in the flow rate, which is considered to increase safety.

Example 2

Subsequently, whether a blood supply flow rate can be controlled to be approximate to a target blood supply flow rate was examined by changing an arterial line pressure using a training device for extracorporeal circulation (Japanese Patent Nos. 3774769 and 4284418) developed by the inventors of the present application.

Figure 11:
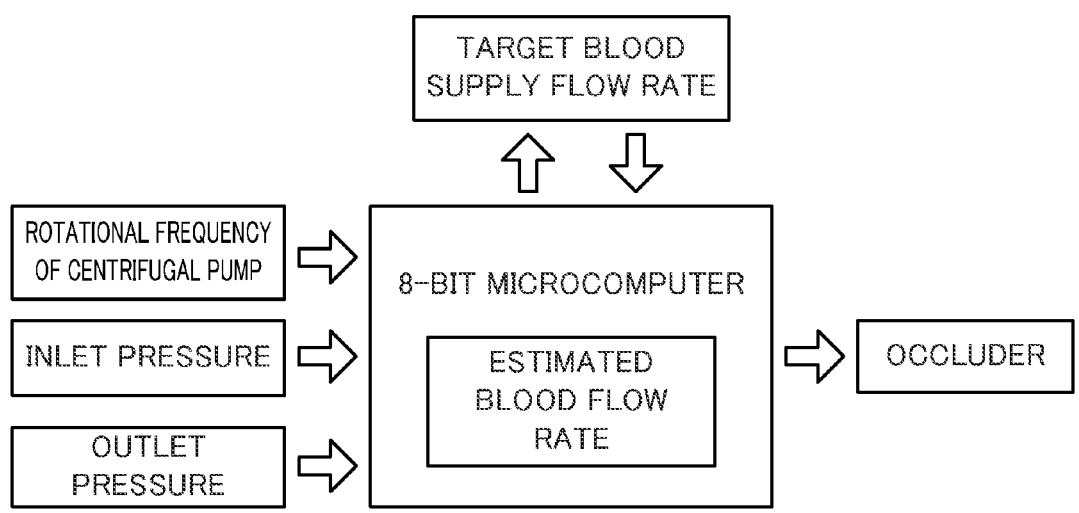
FIG. 11 is a block diagram showing a prototype system used in Example 2.

Initially, a system was prototyped that enabled estimation parameters of an inlet pressure, an outlet pressure, and a rotational frequency of a centrifugal pump to be acquired in real time by an 8-bit microcomputer, an estimated blood flow rate to be calculated by the estimated blood flow rate equation (equation 1) and then the resulting value to be displayed, and an occluder to be controlled. FIG. 11 shows a block diagram of the prototype system.

Figure 3:
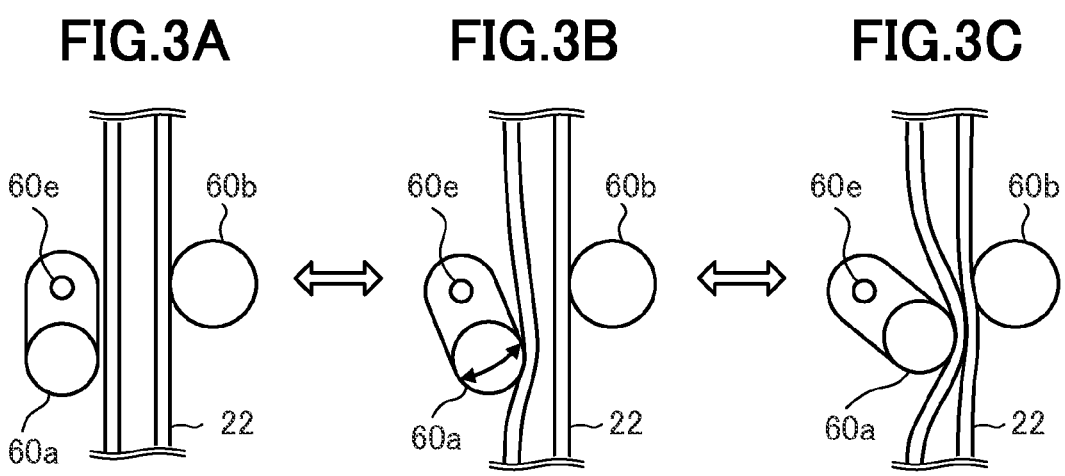
FIGS. 3A, 3B, and 3C show cross sections taken along lines A-A' of FIG. 2.

In addition, a flow rate regulator (occluder) having the structure shown in FIGS. 2 and 3 was prototyped. Then, the prototype system and the occluder were connected to the training device for extracorporeal circulation.

The target blood supply flow rate was entered into the microcomputer by an operator changing a voltage with a volume knob. The target blood supply flow rate was set to 4 L/min.

The rotational frequency of the centrifugal pump was obtained by measuring changes in magnetic flux density with rotation of a magnetic coupling of the centrifugal pump driver by a magnetic sensor (a Hall element) attached to the top of the centrifugal pump. The change in pulsed magnetic flux density was detected three times per revolution for the CAPIOX® centrifugal pump (from Terumo Corporation) used, so that the value was reduced to one-third of the rotational frequency count value to use the resulting value for conversion of the rotational frequency.

Pressure sensors were connected to each of an outlet portion of the centrifugal pump and a level measurement port of a reservoir.

The training device for extracorporeal circulation with the prototype system connected thereto was used, and the arterial line pressure was varied in a predetermined pattern by actuating a control valve for the blood supply flow rate in the training device for extracorporeal circulation. Water (viscosity=about 1 cP) was used as a working fluid.

The blood supply flow rate was regulated by controlling the occluder such that the estimated blood flow rate calculated on the detected rotational frequency, inlet pressure, and outlet pressure of the centrifugal pump was approximate to the entered target blood supply flow rate. Also, the target blood supply flow rate and the estimated blood flow rate were displayed on a display connected to the microcomputer.

Figure 12:
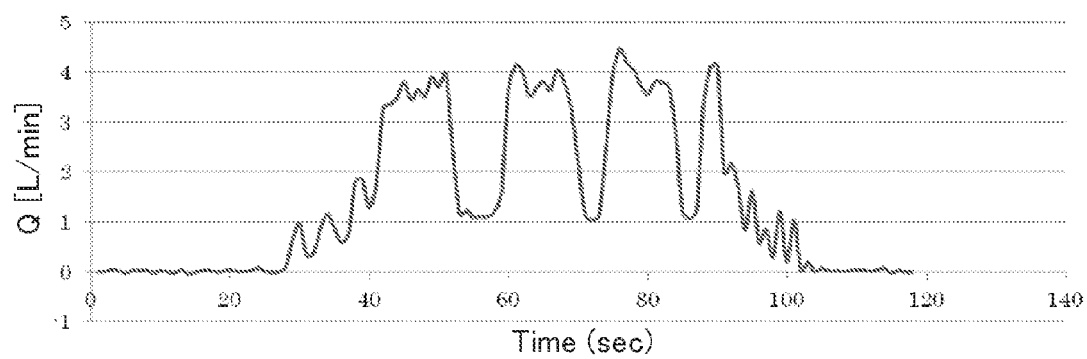
FIG. 12 is a graph showing changes in flow rate without control of the flow rate as in Example 2.

Initially, the arterial line pressure was varied in a predetermined pattern, and then the changes in flow rate without control of the flow rate is shown in FIG. 12. In the experiment, the rotational frequency of the centrifugal pump was gradually increased from 30 sec after the start of the experiment, and then the arterial line pressure was varied with the rotational frequency kept constant when the rotational frequency reached 2000 RPM.

Figure 13:
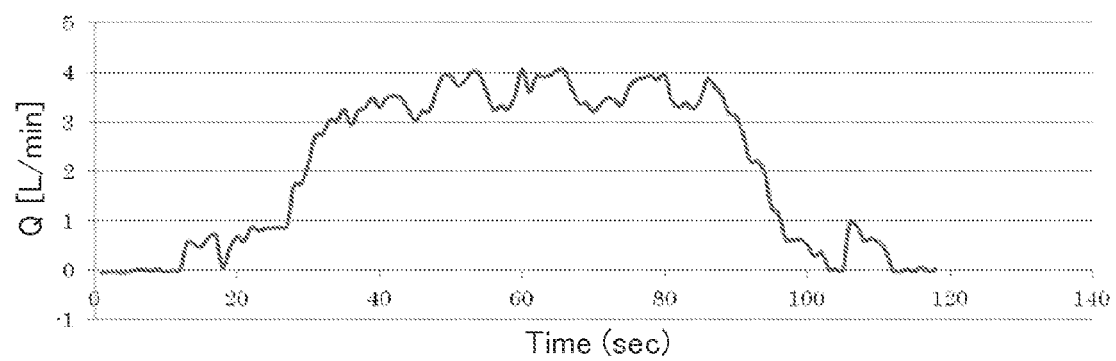
FIG. 13 is a graph showing changes in flow rate when a person with clinical experience manually controlled the flow rate as in Example 2.

Subsequently, the arterial line pressure was varied in the same pattern as above, and then the flow rate was approximate to 4 L/min by a person with clinical experience manually controlling the occluder. FIG. 13 shows the changes in the flow rate.

Figure 14:
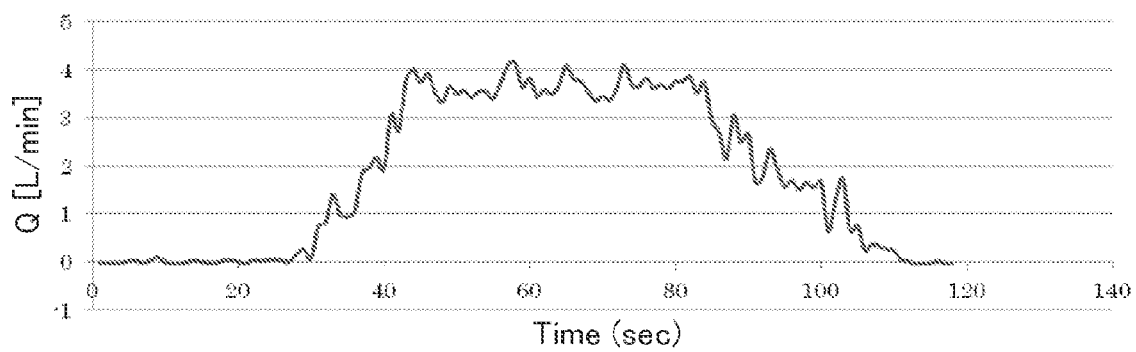
FIG. 14 is a graph showing changes in flow rate when the flow rate is controlled in a prototype system as in Example 2.

Subsequently, the arterial line pressure was varied in the same pattern as above, and then the flow rate was approximate to 4 L/min by the prototype system automatically controlling the occluder. FIG. 14 shows the changes in the flow rate.

FIG. 14 shows that the flow rate is more approximate to 4 L/min than that of FIG. 13. This result confirms that the prototype system can realize high responsivity and stable control of the flow rate compared to the manual control by the person with clinical experience.

The present disclosure can be subject to various embodiments and variations without thereby departing from the scope of the present disclosure. The above embodiments are also intended to illustrate the present disclosure but not to limit the scope thereof.

The present application is based on a Japanese Patent Application No. 2012-053829, filed on Mar. 9, 2012. The entire contents of the specification, the claims, and the drawings of Japanese Patent Application No. 2012-053829 are incorporated herein by reference.

INDUSTRIAL APPLICABILITY

The present disclosure can be utilized in controlling a flow rate of blood passing through an arterial line of an extracorporeal circulation device used in open heart surgery and the like.

REFERENCE SIGNS LIST

1 Artificial heart-lung machine
2 Blood supply flow rate controlling device
10 Living body
20 Blood circulation circuit
21 Venous line
22 Arterial line
30 Reservoir
40 Centrifugal pump
41 Rotational frequency detector
50 Oxygenator
60 Flow rate regulator
60a Pivoting member
60b Fixed member
60c Connecting member
60d Drive source
60e Rotary shaft
70 Filter
81 Inlet pressure detector
82 Outlet pressure detector
90 Controller

The invention claimed is:

1. A blood supply flow rate controlling device for use in an extracorporeal circulation device connected to a living body, the extracorporeal circulation device comprising a centrifugal pump for circulating blood through a blood circulation circuit, the blood supply flow rate controlling device comprising:

rotational frequency detecting means that detects a rotational frequency of the centrifugal pump;

inlet pressure detecting means and outlet pressure detecting means that detect an inlet pressure and an outlet pressure of the centrifugal pump, respectively;

flow rate regulating means that regulates a flow rate of blood supplied to the living body by adjusting a flow path cross section area of the blood circulation circuit; and controlling means that controls the flow rate regulating means, wherein the flow rate regulating means is located downstream of the centrifugal pump, the controlling means comprises an inputter, a storage, a processor, and an outputter, the inputter is configured to receive inputs of a desired target blood supply flow rate entered by an operator, an inlet pressure detection value and an outlet pressure detection value respectively detected by the inlet pressure detecting means and the outlet pressure detecting means, a detected rotational frequency of the centrifugal pump detected by the rotational frequency detecting means, and an estimated blood flow rate equation for calculating an estimated blood flow rate of blood passing through the blood circulation circuit from the inlet pressure detection value, the outlet pressure detection value, and the detected rotational frequency, the storage is configured to store the target blood supply flow rate, the inlet pressure detection value, the outlet pressure detection value, the detected rotational frequency, and the estimated blood flow rate equation, the processor is programmed to calculate a differential pressure by subtracting the inlet pressure detection value from the outlet pressure detection value, the estimated blood flow rate from the differential pressure and the detected rotational frequency by the estimated blood flow rate equation, and a flow rate differential by subtracting the estimated blood flow rate from the target blood supply flow rate, and the outputter is configured to output to the flow rate regulating means a control signal that reduces the flow path cross section area when the flow rate differential has a negative value, a control signal that increases the flow path cross section area when the flow rate differential has a positive value, and a control signal that reduces the flow path cross section area to zero when the estimated blood flow rate has a negative value.

2. The blood supply flow rate controlling device according to claim 1, wherein the estimated blood flow rate equation is expressed by the following equation 1:

$$Qe(f) = \alpha(f) \cdot \Delta P + \beta(f) \quad \text{(equation 1)}$$

where Qe is the estimated blood flow rate, f is the detected rotational frequency of the centrifugal pump, ΔP is the differential pressure by subtracting the inlet pressure detection value from the outlet pressure detection value, and α and β are respectively a slope and an intercept of a linear function of the flow rate of the centrifugal pump as a function of the differential pressure ΔP at the rotational frequency of the centrifugal pump.

3. The blood supply flow rate controlling device according to claim 2, wherein the outputter is configured to output to the flow rate regulating means a control signal that reduces the flow path cross section area to zero when the estimated blood flow rate is above a predetermined threshold flow rate.

4. The blood supply flow rate controlling device according to claim 1, comprising:
a display configured to display the target blood flow rate and the estimated blood flow rate,
the blood supply flow rate controlling device comprising a power supply independent of a power supply to the centrifugal pump.

5. An extracorporeal circulation device comprising the blood supply flow rate controlling device according to claim 1.

* * * * *